United States Patent [19]

Andrieux et al.

[11] 4,207,922

[45] Jun. 17, 1980

[54] LIQUID SAMPLING APPARATUS

[75] Inventors: Claude Andrieux, Orsay; Pierre Renaud, Gif-sur-Yvette, both of France

[73] Assignee: Commissariat a l'Energie Atomique, Paris, France

[21] Appl. No.: 858,946

[22] Filed: Dec. 9, 1977

[30] Foreign Application Priority Data

Dec. 9, 1976 [FR] France ................................ 76 37090

[51] Int. Cl.$^2$ ......................... G01N 1/10; G21C 17/06
[52] U.S. Cl. ........................... 137/625.11; 176/19 LD
[58] Field of Search .............. 137/625.11; 176/19 LD

[56] References Cited

U.S. PATENT DOCUMENTS

| | | | |
|---|---|---|---|
| 3,005,467 | 10/1961 | Suchoza et al. ............ | 176/19 LD X |
| 3,765,461 | 10/1973 | Keck ............................ | 137/625.11 X |
| 3,775,245 | 11/1973 | Delisle et al. .................. | 176/19 LD |
| 3,806,409 | 4/1974 | Debergh et al. ................ | 176/19 LD |

FOREIGN PATENT DOCUMENTS

939965 10/1963 United Kingdom ................ 137/625.11

*Primary Examiner*—Gerald A. Michalsky

[57] ABSTRACT

The invention relates to an apparatus for sampling a liquid conveyed by a plurality of tubes.

The sampling apparatus comprises a cylindrical enclosure with a vertical axis and a circular cross-section having a given length. The enclosure has a lower planar wall, a side wall and a cover which seals the upper part of the enclosure. One of the walls is perforated by a plurality of orifices whose number is at least equal to the number of tubes. The end of each tube issues into one of the orifices which are regularly disposed along a portion of a single curve without a double point. The length of this curve portion exceeds that of the given length. The sampling device also comprises a movable sampling member in the form of a single suction tube having a free end associated with means for simultaneously rotating the suction tube about the axis of the enclosure and for translating the tube in such a way that its free end remains in contact with the wall provided with orifices and moves along the curve.

A particular application is to a system for locating breaks in the jacket of a reactor, particularly a liquid sodium-cooled reactor.

5 Claims, 3 Drawing Figures

LIQUID SAMPLING APPARATUS

BACKGROUND OF THE INVENTION

The present invention relates to an apparatus for sampling a liquid conveyed in a plurality of tubes.

More specifically, the present invention relates to a sampling apparatus forming part of a system for locating a break in a jacket for a reactor and in particular for a liquid sodium-cooled reactor. In such reactors the sealing of the jacket surrounding the fuel elements of the assemblies forming the core is permanently controlled by regularly sampling the cooling liquid from each of the fuel assemblies. For this purpose pipes issue above each of the fuel assemblies. Sampling is carried out by means of a selector which on the one hand permanently samples a mixture of the fluid from all the fuel assemblies, and on the other hand successively takes a sample from each of the tubes.

Numerous different selectors are known. Depending on the particular known construction, they have a base plate into which are welded the ends of the sampling tubes connected to each fuel assembly. In a first construction, these pipes are arranged in accordance with three concentric rings. A suction device having three sampling orifices disposed in accordance with three 120° branches moves in front of the tubes, each orifice permitting samples to be taken from the tubes of one ring. These three samples issue into a mixing box where a secondary selector successively samples one of the three.

Such an apparatus is acceptable in the case where the nuclear reactor only has a relatively limited number of fuel assemblies, that is to say when the selector only has a limited number of sampling tubes. However, such a system could only be used on a more powerful reactor by increasing the number of independent selection devices which necessarily leads to an increase in costs and to an increase in the overall dimensions of such installations placed in the sealing cover of the reactor core whose size is conditioned by the volume of the instrumentation which it must contain.

Selectors are also known in which the tube plate has sampling orifices disposed on a single circle which is concentric to the selector axis. The suction device then passes successively in front of each orifice of the tube plate. Obviously the disadvantage mentioned hereinbefore does not occur; however, for a given enclosure size the number of tubes is necessarily very small.

BRIEF SUMMARY OF THE INVENTION

The problem of the present invention is to provide a selector permitting a considerable increase in the number of liquid samples which can be selected, that is to say the number of tubes reaching said selector for given overall dimensions, whilst permitting the sampling of the liquid from each orifice by means of a single suction tube.

According to the invention, this problem is solved by a sampling apparatus which comprises a cylindrical enclosure with a vertical axis and circular cross-section having a given length l, said enclosure having a lower planar wall, a side wall and a cover which seals the upper part of said enclosure, one of said walls being perforated by a plurality of orifices whose number is at least equal to the number of tubes, whereby the end of each tube issues into one of the orifices, the latter being regularly disposed over a portion of a single curve without a double point, said curve portion having a length exceeding length l, a movable sampling member comprising a single "suction" tube having a free end associated with means for simultaneously rotating said suction tube about the enclosure axis and translating said suction tube in such a way that its free end remains in contact with the wall provided with orifices and moves along the curve.

It is clear that the originality of the invention is based on the fact that the ends of the tubes are disposed on a single curve without a double point which is described by the movable part of the selector, hereinafter called suction device, whereby said movable part always rotates in the same direction in order to take samples from the tube system. This obviates the necessity of having a secondary selector. Moreover, the suction device only passes once in front of a given sampling tube due to the fact that the curve does not have a double point. Thus, this arrangement permits a maximum compactness for a given number of tubes.

According to a first embodiment, said curve is a circular helix of pitch h marked on the side wall of the enclosure, whereby the orifices are regularly spaced over the helix.

In this case the suction tube displacement means comprise a vertical shaft disposed according to the axis of the enclosure integral with a horizontal arm containing the suction tube, the shaft being associated with means for rotating it about said axis and means for translating it at constant speed in accordance with the direction of the axis at a distance equal to h per revolution of the shaft.

Preferably, the translation means comprise a threaded rod disposed in accordance with the axis of the enclosure integral with its lower wall and projecting into the enclosure, the rod cooperating with a tapped blind hole made in the lower end of the shaft.

According to a second embodiment, the curve is a spiral marked on the lower wall of the enclosure, whereby the orifices are regularly spaced on said curve.

In this case, the suction tube displacement means comprise a vertical shaft disposed in accordance with the axis of the enclosure and driving a horizontal arm containing the suction device, the shaft being associated with means for rotating it about the axis and means for translating the first end of the arm in a direction perpendicular to the axis in such a way that the suction device describes the said spiral.

Preferably, the translating means comprise on the one hand a hollow cylindrical body whose axis coincides with said direction, whilst the second end of the arm is forced to move in the cylindrical body, and on the other hand a groove made in the lower wall cooperating with a guidance profile for the suction device.

According to both embodiments at least one of the orifices is not connected to a sampling tube but is instead connected to a pipe whose other end issues into the upper part of the enclosure and the shaft is equipped with a radiating rib disposed within the enclosure and above the arm.

BRIEF DESCRIPTION OF THE DRAWINGS

The invention will be better understood from the following description of two non-limitative embodiments and with reference to the attached drawings, wherein show.

DETAILED DESCRIPTION OF THE PREFERRED EMBODIMENTS

Figure 1:
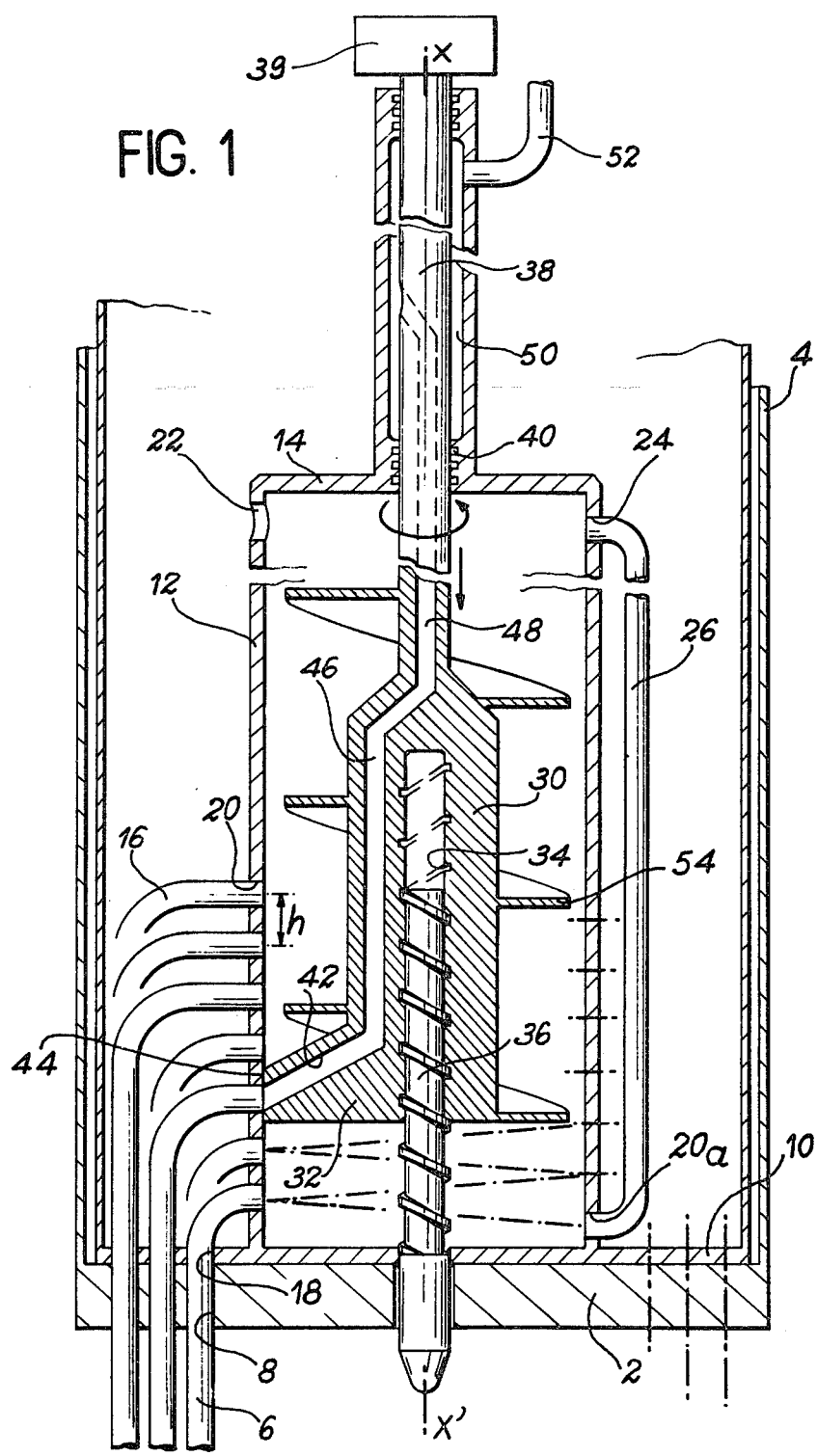
FIG. 1, a vertical sectional view of the first embodiment of the apparatus in which the ends of the sampling tubes are disposed on a circular helix.

As has been stated hereinbefore, in the first embodiment the ends of the sampling tubes (or their extensions) are disposed on a tube plate in accordance with a circular helix. To this end the ends issue into a tube plate shaped like a cylindrical surface with a circular cross-section. The end of the rotary suction device describes a helix which coincides with the helix on which the ends of the sampling tubes are located. Thus, the suction device moves successively in front of the end of each sampling tube.

The actual selector is placed within an enclosure constituted by a base plate 2 and a cylindrical wall 4. The circumference of the base plate and therefore the length of the side wall is equal to 1. It is further pointed out that the sampling tubes such as 6 are welded at their upper end into bores such as 8 provided in base plate 2. The actual selector comprises a flat base 10 which rests on base plate 2. Flat base 10 with cylindrical side wall 12 and cover 14 constitutes a cylindrical mixing box having a circular cross-section and vertical axis XX'. At the same time side wall 12 constitutes the tube plate of the selector. Each sampling tube is connected to a bent tube such as 16, one of whose ends is connected to a sampling tube 6 passing through the flat base by bores such as 18 and which is connected by its other end to side wall 12 (or tube plate) in bores such as 20. It is therefore at bores 20, i.e. the ends of bent tubes 16, that the cooling liquid is successively sampled. In general terms and from an operational standpoint, it can be considered that the sampling tubes comprise on the one hand tubes 6 and on the other their bent extensions 16. h is the vertical pitch of the helix on which are disposed the bores 12 and R is the radius of side wall 12 ($l=2\pi R$).

The mixing box is equipped with orifices such as 22 disposed in the upper part of side wall 12. The sodium leaving bent tube 16 is discharged via said orifices. One orifice 20, carrying for example the reference numeral 20a, is not connected to a sampling tube being instead connected to an orifice 24 in the upper portion of the mixing box by a pipe 26 located on the outside of the mixing box. However, orifice 20a is still disposed on the helix. Thus, at the outlet from pipe 26, i.e. at orifice 20a, a mixture of the sodium contained in the mixing box is available, that is to say a mixture of all the samples made in the various fuel assemblies.

The movable part of the selector comprises a rotary sampler which is essentially formed by a cylindrical member 30 equipped with a sampling arm 32. Cylindrical member 30 has a tapped blind bore 34 at its lower end and in accordance with its vertical axis XX'. The tapped bore cooperates with a vertical threaded shaft 36 fixed to flat base 10. Cylindrical member 30 is extended by a vertical control shaft 38 which sealingly traverses cover 14 of the mixing box by means of a sealing system 40 which also serves as a bearing.

At its upper end control shaft 38 is fixed to a motor 39 which rotates the latter about axis XX'. Member 30 and therefore also arm 32 are rotated. Thread tapping 34 and thread 36 have the same pitch as the helix on which are arranged the ends 20 of bent tubes 16, i.e. a pitch equal to h. Thus, when control shaft 38 is rotated, arm 32 rotates about axis XX' and at the same time moves vertically under the action of thread 36. Arm 32 moves successively in front of each of the orifices 20 (and in front of orifice 20a). Arm 32 is equipped with an inner pipe 42 which issues at the end of arm 32 into a face constituted by a cylindrical surface portion 44 which is sealingly displaced along said wall 12. Pipe 42 is extended by pipe 46 within member 30 and is continued by a duct 48 made in control shaft 38. This duct issues into an annular chamber 50 which surrounds the shaft and is connected to a sampling pipe 52 which in turn passes to a detection or metering apparatus.

The cylindrical member 30 of the selector is also peripherally provided with a rib such as 54 permitting the stirring of the liquid metal within the mixing box 12.

The operation of the apparatus can be clearly gathered from the preceding description. At the outlet from bent tube 16, i.e. at orifices 20 there is a continual sampling of the cooling liquid in each of the fuel assemblies, except in orifice 20a where there is a liquid sampled from the mixing box, i.e. the liquid which enters said orifice is representative of all the samples taken by the sampling tubes arriving at orifice 20a. Due to the presence of a rib 54 which ensures homogeneous mixing, the sample is truly representative of said mixture. By operating a not shown driving motor of control shaft 38 the end of pipe 42 of arm 32 is successively and regularly displaced in front of each of the orifices 20, whereby the end of pipe effectively describes the helix on which are located orifices 20 due to the pitch value of threaded shaft 36.

For example, in the case of a base plate with a diameter of 400 mm, sampling can be carried out in 225 sampling tubes 6 of conventional diameter for this type of sampling operation.

Figure 2:
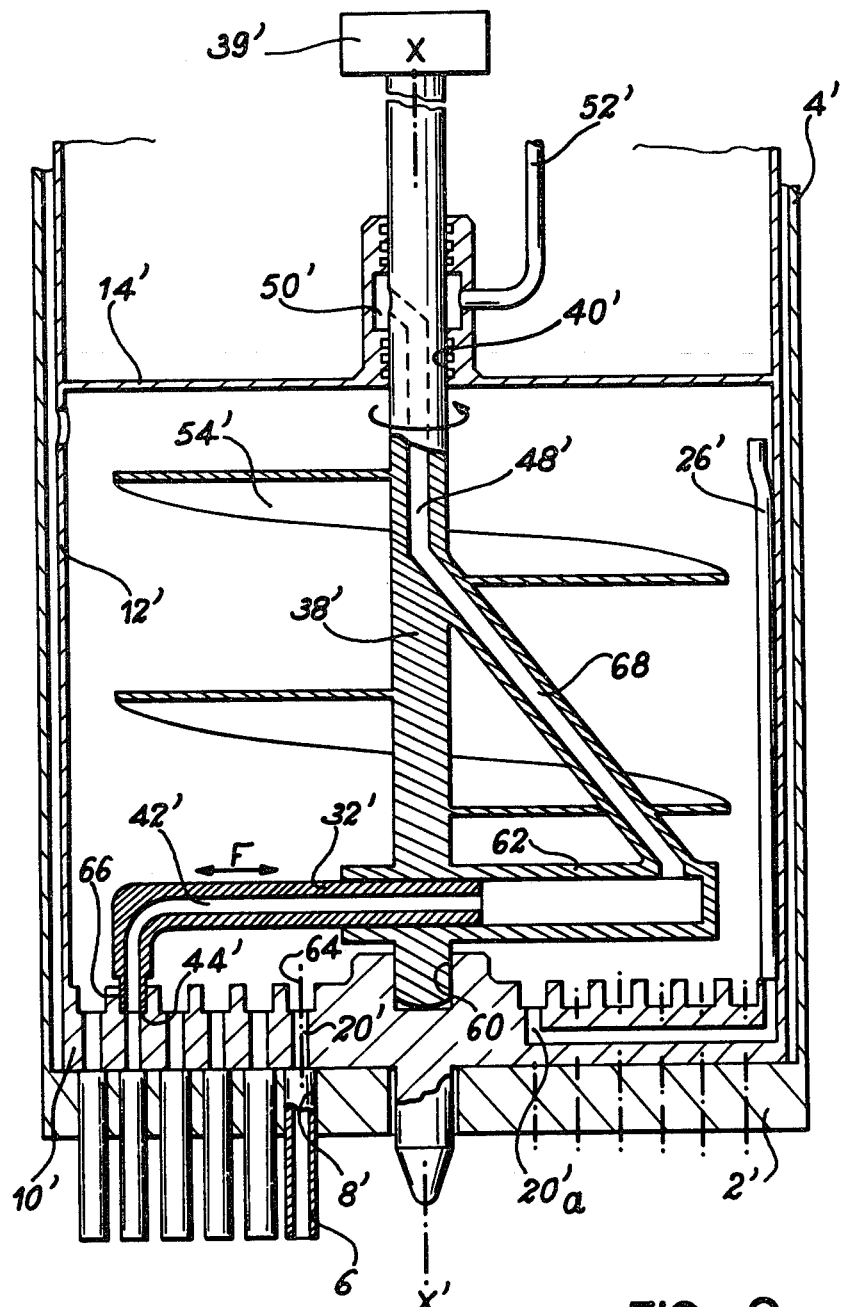
FIG. 2, a vertical sectional view of the second embodiment of the invention in which the ends of the sampling tubes are disposed on a spiral.
Figure 3:
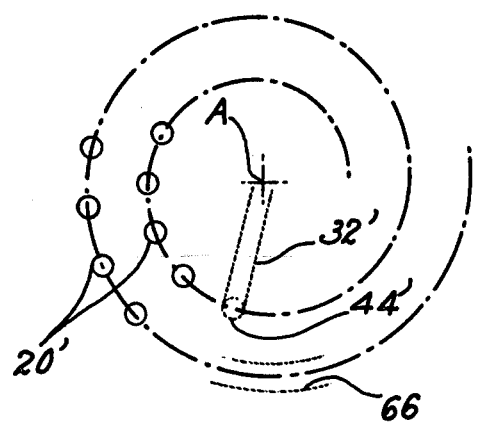
FIG. 3, a diagrammatic plan view of the apparatus of FIG. 2 showing the arrangement of the ends of the tubes in the lower tube plate.

FIGS. 2 and 3 show a second embodiment of the selector in which the ends of the sampling tubes are disposed on a spiral. In other words, there is in this case a planar curve instead of the ends of the sampling tubes being disposed on a curve in space.

In this embodiment there is a base plate 2' perforated by a certain number of bores 8' in which are welded the upper ends of sampling tubes 6. The actual selector comprises a flat base 10' which in this embodiment also acts as a tube plate. The mixing box is completed by cylindrical side wall 12' of length l and by cover 14'. The flat base 10' is perforated by a plurality of bores 20' which have precisely the same arrangement as the ends of the sampling tubes, i.e. the same as bores 8' in base plate 2'. As can be seen in FIG. 3, bores 20' are arranged in accordance with a spiral formed from a central point A which coincides with the vertical axis XX' of the selector. The length of the spiral portion on which are arranged the bores 20' is therefore slightly greater than l. However, one of the orifices 20' carrying the reference 20'a has the function of supplying a mixture of the samples in the various fuel assemblies and not a sample of the cooling liquid from a single given fuel assembly. To this end orifice 20'a is connected to the upper part of mixing box 12' by pipe 26' which issues into the upper part of mixing box 12'. Thus, the fixed part of the selector has been defined. The movable part of the selector comprises a vertical control shaft 38' arranged in the axis XX' of the selector. The lower part of the shaft cooperates with a centreing and guidance bore 60 made in the base 10', whilst its upper part traverses cover 14' in a sealed manner as a result of the sealing device 40' equipped with baffles, and which at the same time serves as the bearing. The upper part of the shaft is rotated about axis XX' by a motor system 39'. The lower end of shaft 38' is equipped with an arm 32' slidingly mounted in a hollow cylindrical body 62 having a horizontal axis. The cylindrical body 62 is rotated by control shaft 38'. Arm 32' is provided with an inner pipe 42' issuing at one of its ends on the outer face of the suction device 44', whereby at its other end pipe 42' issues into cylindrical body 62 which is rotated about axis XX'. Thus, the same happens to arm 32'. In addition, the displacements of arm 32' in accordance with its axis, i.e. in horizontal directions are guided by the cooperation of a groove 64 in flat base 10' whereby said groove is spiral-shaped and orifices 20' issuing into the bottom of the groove, with the end 44' of arm 32' provided with a reduced diameter guidance end 66.

It is therefore obvious that on rotating control shaft 38' arm 32' rotates about axis XX' and slides in the direction of the axis of pipe 42', i.e. in the direction F in the drawing. Therefore end 44' of the suction device describes the complete spiral on which are disposed orifices 20'.

Control shaft 38' also has an inner pipe 68 which connects the inside of hollow cylindrical body 62 to an axial bore 48' in shaft 38'. Bore 48' issues into an annular space 50' fixed to cover 14', said bore 50' itself being connected to a pipe 52' which conveys the sampled liquid to a not shown measuring and detecting apparatus.

Control shaft 38' is also equipped with a rib 54' which stirs the liquid in the mixing box and consequently the sample which reaches orifice 20'a is a truly representative sample of all the fluid sampled from all the fuel assemblies.

In both cases when the end of the movable arm has described the complete spiral or helix the centre of rotation of the control shaft is reversed so that the helix or spiral is then described again in the reverse direction.

It is readily apparent that one of the most significant features of such systems is that sampling can be performed relative to a random number of tubes. In the present case there are 225 tubes, whereby, for example, in the case of the embodiment of FIG. 2 the 225 tubes are distributed over a spiral with seven turns, i.e. to carry out sampling in all the tubes the control shaft must revolve seven times. Another advantage of these two embodiments is that the marking of the sampling tube in which sampling is being carried out is very simple because it is merely necessary to provide a revolution counter and an angular reference marking device in order to differentiate the various tubes corresponding to the same revolution.

The invention is not limited to the embodiments described and represented hereinbefore and various modifications can be made thereto without passing beyond the scope of the invention.

What is claimed is:

1. An apparatus for sampling a liquid in a plurality of tubes wherein it comprises a cylindrical enclosure with a vertical axis and circular cross-section having a given length l, said enclosure having a lower planar wall, a side wall and a cover which scales the upper part of the enclosure, the lower planar wall being perforated by a plurality of orifices whose number is at least equal to the number of tubes, the end of each tube issuing into one of the orifices, the orifices being regularly disposed on a spiral marked on the lower planar wall, and a movable sampling member comprising a single suction tube having a free end associated with means for simultaneously rotating the suction tube about the axis of the enclosure and translating the tube in such a way that its free end remains in contact with the wall provided with orifices and moves along the curve.

2. An apparatus according to claim 1, wherein the suction tube displacement means comprise a vertical shaft disposed in accordance with the axis of the enclosure and driving a horizontal arm containing the suction tube, the shaft being associated with means for rotating it about the axis and means for translating the first end of the arm in a direction perpendicular to the axis in such a way that the free end of the suction tube describes the said spiral.

3. An apparatus according to claim 2, wherein the translating means comprise on the one hand a hollow cylindrical body whose axis coincides with said direction, whilst the second end of the arm is forced to move in the cylindrical body, and on the other hand a groove made in the lower wall cooperating with a guidance profile for the suction device.

4. An apparatus according to claim 2, wherein the shaft is equipped with a radiating rib disposed within the enclosure and above the arm.

5. An apparatus according to claim 1, wherein at least one of the orifices is not connected to a sampling tube and is instead connected to a pipe whose other end issues into the upper part of the enclosure.

* * * * *